US008926698B2

(12) United States Patent
Wollnick et al.

(10) Patent No.: US 8,926,698 B2
(45) Date of Patent: Jan. 6, 2015

(54) MOLDABLE BACK BREAST FORM

(71) Applicant: American Breast Care, LP, Marietta, GA (US)

(72) Inventors: Amanda Wollnick, Doraville, GA (US); Robert Halley, Atlanta, GA (US)

(73) Assignee: American Breast Care, LP, Marietta, GA (US)

( * ) Notice: Subject to any disclaimer, the term of this patent is extended or adjusted under 35 U.S.C. 154(b) by 211 days.

(21) Appl. No.: 13/678,750

(22) Filed: Nov. 16, 2012

(65) Prior Publication Data

US 2013/0131798 A1 May 23, 2013

Related U.S. Application Data

(60) Provisional application No. 61/561,004, filed on Nov. 17, 2011, provisional application No. 61/644,096, filed on May 8, 2012.

(51) Int. Cl.
*A61F 2/12* (2006.01)
*A61F 2/52* (2006.01)

(52) U.S. Cl.
CPC .... *A61F 2/12* (2013.01); *A61F 2/52* (2013.01)
USPC .......................................................... 623/7

(58) Field of Classification Search
USPC ....................................................... 623/7–8
See application file for complete search history.

(56) References Cited

U.S. PATENT DOCUMENTS

| 5,158,573 | A | * | 10/1992 | Berg | 523/113 |
|---|---|---|---|---|---|
| 5,525,275 | A | | 6/1996 | Iversen et al. | |
| 6,660,204 | B1 | * | 12/2003 | Clover et al. | 264/222 |
| 7,575,596 | B2 | * | 8/2009 | Bowman et al. | 623/7 |
| 7,753,954 | B2 | | 7/2010 | Tassone et al. | |
| 2005/0256572 | A1 | | 11/2005 | Wild | |
| 2012/0071973 | A1 | * | 3/2012 | Rechenberg | 623/8 |
| 2012/0277860 | A1 | | 11/2012 | Dvir et al. | |

OTHER PUBLICATIONS

KIPO: "Notification of Transmittal of the International Search Report and the Written Opinion of the International Searching Authority, or the Declaration" Jan. 22, 2014.

* cited by examiner

*Primary Examiner* — Suzette J Gherbi
(74) *Attorney, Agent, or Firm* — Bryan W. Bockhop; Bockhop & Associates, LLC

(57) ABSTRACT

A breast prosthesis for wearing against a chest of a user includes a bag, a first silicone rubber and a silicone agglomerate putty. The bag includes at least three films that are sealed together around a periphery so as to define at least a front chamber and a back chamber. The first silicone rubber is disposed in the front chamber and is cured in an outer shape of a breast. The silicone agglomerate putty is disposed in the back chamber and is configured as a shear thinning fluid that conforms in shape to surface features of the chest of the user when placed against the chest of the user.

20 Claims, 1 Drawing Sheet

MOLDABLE BACK BREAST FORM

CROSS-REFERENCE TO RELATED APPLICATION(S)

This application claims the benefit of U.S. Provisional Patent Application Ser. Nos. 61/561,004, filed Nov. 17, 2011, and 61/644,096, filed May 8, 2012, the entirety of each of which is hereby incorporated herein by reference.

BACKGROUND OF THE INVENTION

1. Field of the Invention

The present invention relates to breast prostheses and, more specifically, to a breast prosthesis that adapts to a surface against which it is placed.

2. Description of the Related Art

A breast prosthesis is an object that is used to appear like a natural breast that has been removed by a mastectomy. Some breast prosthesis wearers desire an external breast prosthesis that conforms to any surface irregularities or sensitive scar tissue created on the chest wall by a mastectomy. A more comfortable and secure fit is achieved by a breast prosthesis that conforms to these surface irregularities, as the breast prosthesis will protect and cushion these sensitive areas.

There are several types of external breast prostheses designed to adapt to surface irregularities on the chest wall. One type is produced by custom molding the breast prosthesis for the wearer. However, this method is not cost effective and may not be available to all wearers. Another type of breast prosthesis has a very soft, cross-linked silicone gel as the inner layer. This soft gel conforms somewhat to the chest wall of the wearer when worn but the elastic properties of a crosslinked gel limit its ability to conform. Another type of breast prosthesis has a self-shaping dispersion as the inner layer. The self-shaping dispersion typically includes a silicone oil, microspheres, and thixotropic agents and stabilizers. However, over time, these components tend to separate, which requires the wearer to massage the inner layer to reincorporate the components.

Some breast prosthesis wearers desire an external breast prosthesis that conforms to surface irregularities or scar tissue created on the chest wall by a mastectomy. A more comfortable and secure fit would be achieved by a breast prosthesis that conforms to these surface irregularities. However, existing breast prostheses fail to conform adequately to such surface irregularities.

Therefore, there is a need for a breast prosthesis to conforms to an irregular surface.

SUMMARY OF THE INVENTION

The disadvantages of the prior art are overcome by the present invention which, in one aspect, is a breast prosthesis for wearing against a chest of a user that includes a bag, a first silicone rubber and a silicone agglomerate putty. The bag includes at least three films that are sealed together around a periphery so as to define at least a front chamber and a back chamber. The first silicone rubber is disposed in the front chamber and is cured in an outer shape of a breast. The silicone agglomerate putty is disposed in the back chamber and is configured as a shear thinning fluid that conforms in shape to surface features of the chest of the user when placed against the chest of the user.

In another aspect, the invention is a breast prosthesis for wearing against a chest of a user. Two films are sealed together around a periphery so as to define chamber therebetween. A silicone agglomerate putty is disposed in the chamber and is configured as a shear thinning fluid that conforms in shape to surface features of the chest of the user when placed against the chest of the user.

In yet another aspect, the invention is a method of making a breast prosthesis, in which at least three films are sealed together around a periphery so as to form a bag that defines at least a front chamber and a back chamber. A silicone agglomerate putty that maintains a shape when not subjected to shear forces and that deforms in response to shear forces is made. A first silicone rubber is injected into the front chamber. The silicone agglomerate putty is injected into the back chamber. The first silicone rubber is cured in the form of an outer shape of a breast.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

Figure 1:
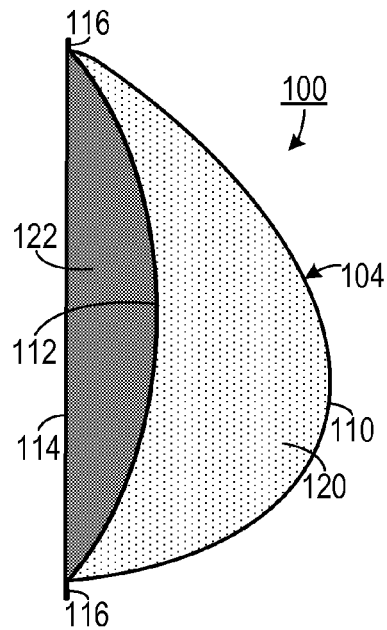
FIG. 1 is a schematic diagram on one embodiment of a breast prosthesis.

A preferred embodiment of the invention is now described in detail. Referring to the drawings, like numbers indicate like parts throughout the views. Unless otherwise specifically indicated in the disclosure that follows, the drawings are not necessarily drawn to scale. As used in the description herein and throughout the claims, the following terms take the meanings explicitly associated herein, unless the context clearly dictates otherwise: the meaning of "a," "an," and "the" includes plural reference, the meaning of "in" includes "in" and "on."

Figure 2A:
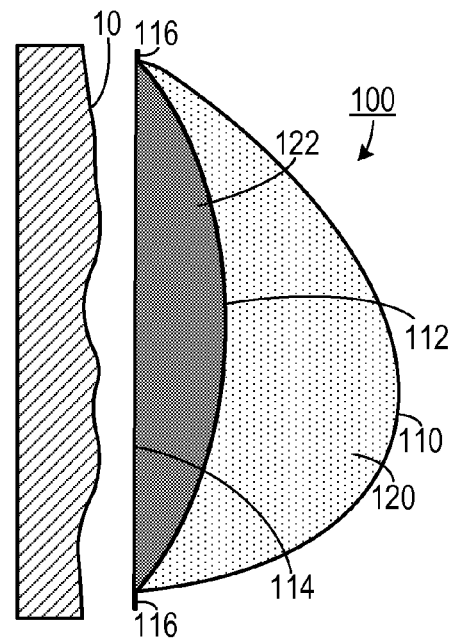
FIGS. 2A-2C are a series of schematic diagrams of a breast prosthesis placed against an irregular surface.
Figure 2B:
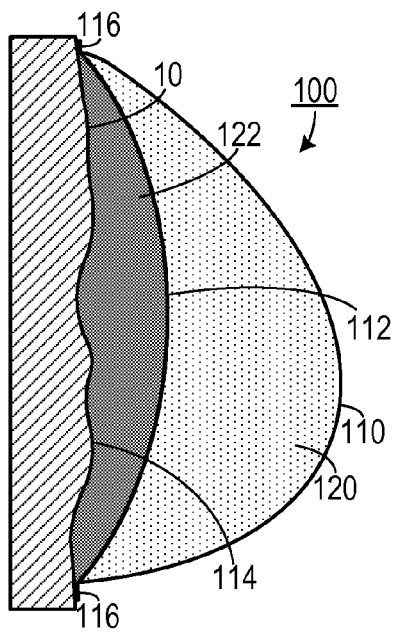
Figure 2C:
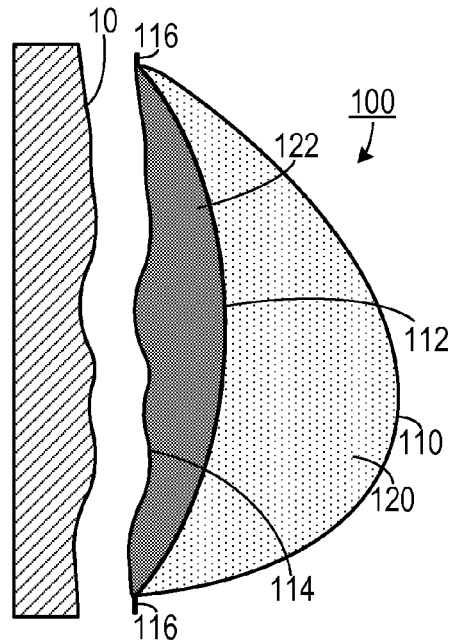

As shown in FIGS. 1 and 2A-2C, one embodiment of a breast prosthesis 100 includes a two-chambered bag 104 formed from a first film 110, a second film 112 and a third film 114 that are heat sealed together about their periphery 116. (The films could include polyurethane.) The chamber between the first film 110 and the second film 112 is filled with a cross-linked silicone rubber 120 that has been molded and cured in a shape corresponding to the outer shape of a breast. The chamber between the second film 112 and the third film 114 is injected with a silicone agglomerate putty 122 that has the properties of a shear thinning fluid. As used herein, a shear tinning fluid is a substance that is deformable in response to a shear force, but that maintains its shape when not subjected to a shear force. Also as used herein, a silicone agglomerate putty is a material that includes silicone and that has physical properties of a shear thinning fluid. Thus, when placed against an uneven surface 10 (such as a user's chest with scar tissue), the silicone agglomerate putty 122 conforms to the irregular surface 10 and maintains the shape of the irregular surface 10 until it is applied to a surface having a different shape. Because of this property, the silicone agglomerate putty 122 conforms in shape to surface features of the chest of the user, which can make the breast prosthesis 100 more comfortable to wear. In one embodiment, the silicone agglomerate putty 122 includes an agglomerate of finely ground silicone rubber particles that are swollen with a liquid, such as: a silicone oil, a non-silicone oil, an alcohol, an ester or a similar substance. The swollen silicone rubber particles adhere to each other so as to behave like a putty. However, the particles are moveable relative to each other when the putty is subjected to a shear force.

In one representative embodiment, the silicone agglomerate putty 122 is made by grinding a stiff silicon rubber into a plurality of finely ground silicone rubber particles. A liquid, such as a silicone oil, is added to the finely ground silicone rubber particles, causing them to swell. The finely ground silicone rubber particles are mixed with the oil until the mixture becomes a shear thinning fluid.

In one embodiment, the silicone oil used in the silicone agglomerate putty has a viscosity in a range of 0.65 centistokes to 10,000 centistokes. Some typical embodiments will use a silicone oil that has a viscosity in a range of 10 centistokes to 500 centistokes. Generally, using a silicone oil of higher viscosity will require relatively less oil and using a silicone oil of lower viscosity will require relatively more oil. However, silicone oils may be be less expensive than the other precursor components and, therefore, the use of more silicone oil might result in a less expensive silicone agglomerate putty.

In one experimental embodiment the silicone agglomerate putty was made by first making a stiff silicone elastomer rubber by using a 100 centistoke silicone oil and a vinyl polymer liquid in a ratio of about two parts by weight silicone oil to one part vinyl polymer liquid. A platinum catalyst in an amount of 0.04% to 0.05% of the total weight was added and a cross-linker (such as XL-18, available from AB Specialty Silicones) was also added. The combination was mixed together and allowed to cure under heat. Once cooled, the resulting stiff silicone rubber was cut into approximately one inch cubes and was ground into a plurality of silicone particles with an average diameter of about 1 mm in a shear force mixer (which in this experimental embodiment was a food processor). A 100 centistoke silicone oil was added in a weight ratio that roughly equaled the weight of the plurality of silicone particles and the combination was mixed in the shear force mixer until the combination had the properties of a shear thinning fluid.

In another representative embodiment, the silicone agglomerate putty is made by first combining a plurality of silicone rubber precursor components, which may include a vinyl polymer, a cross-linker, a silicone oil and a catalyst. In this embodiment, the silicone oil is in a concentration that is in a range between 70% and 90% by weight. Microspheres that are selected to make the agglomerate putty lighter may also be added at this stage. In such a case, microspheres having a lower density that the overall density of the silicone agglomerate putty are selected. Similarly, a pigment may also be added at this stage. The precursor components are mixed in a planetary mixer at room temperature. The precursor components cure while being mixed and the planetary mixer breaks apart the silicone rubber that forms during the mixing, resulting in the agglomerate putty.

In one embodiment, a double planetary mixer (such as one available from Charles Ross & Son Company) can be used. In this embodiment, the double planetary mixer is coupled with a discharge system such that the silicone agglomerate putty, which is a non-flowing material, can be removed from the mixing vessel and be dispensed into the back chamber of the breast form. Other mixing equipment may also be employed to mix the silicone agglomerate putty, including: single or multiple screw extruders, dynamic or static mixers, colloid mills, homogenizers, and sonolators.

Another experimental embodiment started with about 16%-17% vinyl polymer liquid, about 0.8% cross-linker, about 0.05% platinum catalyst and about 82.5% 100 centistoke silicone oil. All of these precursors were mixed in a planetary mixer and the silicone cured at room temperature while being mixed. The mixing was done at low speed and lasted for about one hour, with the result that the silicone agglomerate putty was formed. In other embodiments, mixing lasted for between one and three hours.

In another embodiment, the silicone oil is in a concentration that is in a range between 20% and 50% by weight. In this embodiment, the mixer mixes the precursor components until a cured silicone powder is formed. A liquid (such as a silicone oil) is added to the cured silicone powder, causing the cured silicone particles to swell and form the combination is mixed to form the shear thinning fluid.

In making the breast form, the addition-vulcanizing silicone rubber components may be injected into the outer chamber and the middle chamber (in a three-chamber embodiment) and the silicone agglomerate putty is injected into the back chamber. Typically, the injection of these materials is done while the bag is inside a breast form mold so that the injected materials and the bag fill the mold. The mold is then placed in an oven and the silicone rubber components are cured. Since the silicone agglomerate putty includes components that are already cured, the heating of the putty will not change it. Once cured, the mold is removed and allowed to cool. Once cool, the periphery of the bag is trimmed and the resulting breast prosthesis is packaged.

In one embodiment, lightweight silicone can be ground into a powder and swollen with silicone oil to make a lightweight agglomerate putty. Additionally, other silicone fluids or solvents could be used to swell the powder. Other additives could be added to the gel or the swelling fluid to give the agglomerate putty potential cooling properties. Additionally, the silicone could be cured in water while mixing and, once the silicone putty is cured, the water is evaporated off.

In one embodiment, the bag includes four films that are sealed along the periphery so as to form a front chamber, a middle chamber and a back chamber. The front chamber includes a lightweight silicone rubber that is cured so as to have the shape of a breast. The middle chamber includes a denser firm silicone rubber that is cured and that provides support for the breast form. The back chamber includes the silicone agglomerate putty.

U.S. Pat. No. 7,753,954, filed by Tassone et al., discloses methods of making a two-chamber breast prosthesis employing silicone rubber and is incorporated herein by reference. US Patent Application Publication No. US-2012-0071973-A1, filed by Recheberg, discloses methods of making a three-chamber breast prosthesis employing silicone rubber and is also incorporated herein by reference.

One embodiment includes two films that are sealed together around a periphery so as to define chamber therebetween and a silicone agglomerate putty that is disposed in the chamber. This single chamber embodiment does not employ an outer chamber of cured silicone rubber, but its outer shape can be custom-formed by the user each time it is used. It could be useful, for example, to fill in indentations in a breast due to a lumpectomy.

Using a swollen silicone rubber powder agglomerate putty has several advantages. For example, it forms a soft and pliable agglomerate putty that can easily be conformed to the unique shape of the wearer's chest wall. Since it lacks elastic properties, the agglomerate putty will hold these shapes until additional forces are applied to it. The agglomerate putty does not pool in the bottom of the breast prosthesis. There is no separation of the silicone powder out of its solution, since it absorbs the solution via swelling. Additionally, the silicone powder can be a lightweight silicone powder and can be pigmented. The ultimate properties of the powder are based upon the silicone from which it was made. The consistency of the agglomerate putty can be readily modified by adjusting the size of the silicone rubber powder particles, the amount of silicone oil used to swell the powder, the type of silicone fluid used, or the addition of other solvents such as aromatic hydrocarbons, aliphatic hydrocarbons, alcohols, aldehydes, ketones, amines, esters, ethers, glycols, glycol ethers, alkyl halides, or aromatic halides, to swell the silicone powder.

In one embodiment, the silicone agglomerate putty can be a thermoreversible gel that is liquefied at a certain temperature not corresponding to body temperature and that takes the properties of a gel at body temperature. Such a gel can be made with an aqueous, nonionic triblock copolymer. This particular gel is not cross linked nor does it consist of a liquid with thickening agents. The nonionic triblock copolymer is dissolved in an aqueous solution. At particular temperatures, the nonionic triblock copolymer remains dissolved in the solution, in a liquid state. At room temperature or body temperature, the nonionic triblock copolymers aggregate to form micelles, which give the gel its moldable consistency. In one embodiment, the thermoreversible gel includes an aqueous, nonionic triblock copolymer solution. However other materials may also be used. For example a thermoreversible gel could include a mineral oil or silicone oil as the continuous phase using an appropriate polymer surfactant as a gelling agent. The following are examples of suitable materials: Siltech Multi Domain™ Silicones—alkyl dimethicone polymers in mineral oil and alkyl dimethicone polymers in silicone oil gels of polyethylene block copolymers and liquid hydrocarbons.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A breast prosthesis for wearing against a chest of a user, comprising:
    (a) a bag that includes at least three films that are sealed together around a periphery so as to define at least a front chamber and a back chamber;
    (b) a first silicone rubber disposed in the front chamber and cured in an outer shape of a breast; and
    (c) a shear thinning fluid silicone agglomerate putty that is disposed in the back chamber and that conforms in shape to surface features of the chest of the user when placed against the chest of the user.

2. The breast prosthesis of claim 1, wherein the bag further comprises a fourth film so that the bag defines a middle chamber, a second silicone rubber, different from the first silicone rubber, disposed in the middle chamber.

3. The breast prosthesis of claim 2, wherein the first silicone rubber comprises a lightweight silicone rubber and wherein the second silicone rubber comprises a firm silicone that is configured to provide support to the breast prosthesis.

4. The breast prosthesis of claim 1, wherein the shear thinning fluid silicone agglomerate putty comprises an agglomerate of finely ground silicone rubber particles swollen with a liquid.

5. The breast prosthesis of claim 4, wherein the liquid comprises a liquid selected from a list consisting of: a silicone oil, a non-silicone oil, an alcohol, an ester, and combinations thereof.

6. The breast prosthesis of claim 1, wherein the shear thinning fluid silicone agglomerate putty has a first density and wherein the silicone agglomerate putty further comprises microspheres that have a second density that is less than the first density.

7. The breast prosthesis of claim 1, wherein the shear thinning fluid silicone agglomerate putty further comprises a pigment.

8. The breast prosthesis of claim 1, wherein the bag comprises a polyurethane film.

9. A breast prosthesis for wearing against a chest of a user, comprising:
    (a) two films that are sealed together around a periphery so as to define chamber therebetween; and
    (b) a shear thinning fluid silicone agglomerate putty that is disposed in the chamber and that conforms in shape to surface features of the chest of the user when placed against the chest of the user.

10. The breast prosthesis of claim 9, wherein the two films comprise polyurethane film.

11. The breast prosthesis of claim 9, wherein the shear thinning fluid silicone agglomerate putty comprises an agglomerate of finely ground silicone rubber particles swollen with a liquid.

12. The breast prosthesis of claim 11, wherein the liquid comprises a liquid selected from a list consisting of: a silicone oil, a non-silicone oil, an alcohol, an ester, and combinations thereof.

13. The breast prosthesis of claim 9, wherein the shear thinning fluid silicone agglomerate putty has a first density and wherein the silicone agglomerate putty further comprises microspheres that have a second density that is less than the first density.

14. The breast prosthesis of claim 9, wherein the shear thinning fluid silicone agglomerate putty further comprises a pigment.

15. A breast prosthesis for wearing against a chest of a user, comprising:
    (a) a bag that includes at least three polyurethane films that are sealed together around a periphery so as to define at least a front chamber and a back chamber;
    (b) a first silicone rubber disposed in the front chamber and cured in an outer shape of a breast; and
    (c) a shear thinning fluid silicone agglomerate putty that is disposed in the back chamber and that is configured as a shear thinning fluid that conforms in shape to surface features of the chest of the user when placed against the chest of the user, wherein the silicone agglomerate putty comprises an agglomerate of finely ground silicone rubber particles swollen with a liquid.

16. The breast prosthesis of claim 15, wherein the bag further comprises a fourth film so that the bag defines a middle chamber, a second silicone rubber, different from the first silicone rubber, disposed in the middle chamber.

17. The breast prosthesis of claim 15, wherein the first silicone rubber comprises a lightweight silicone rubber and wherein the second silicone rubber comprises a firm silicone that is configured to provide support to the breast prosthesis.

18. The breast prosthesis of claim 15, wherein the liquid comprises a liquid selected from a list consisting of: a silicone oil, a non-silicone oil, an alcohol, an ester, and combinations thereof.

19. The breast prosthesis of claim 15, wherein the silicone agglomerate putty has a first density and wherein the silicone agglomerate putty further comprises microspheres that have a second density that is less than the first density.

20. The breast prosthesis of claim 15, wherein the silicone agglomerate putty further comprises a pigment.

* * * * *